(12) United States Patent
Anabalón Alamos et al.

(10) Patent No.: US 9,604,029 B2
(45) Date of Patent: Mar. 28, 2017

(54) EMULATION OF SENSORY STIMULI, EMANATING FROM A REFERENCE PERSON, FOR A CHILD

(71) Applicant: Babybe GmbH, Aichtal (DE)

(72) Inventors: Camilo Andres Anabalón Alamos, Stuttgart (DE); Raphael Patrick Manfred Lang, Aichtal (DE)

(73) Assignee: Baybe GmbH, Aichtal (DE)

( * ) Notice: Subject to any disclaimer, the term of this patent is extended or adjusted under 35 U.S.C. 154(b) by 0 days.

(21) Appl. No.: 14/270,059

(22) Filed: May 5, 2014

(65) Prior Publication Data

US 2014/0330070 A1  Nov. 6, 2014

(30) Foreign Application Priority Data

May 3, 2013  (EP) .................................... 13166341

(51) Int. Cl.
*A61M 21/02*  (2006.01)
*A61B 5/113*  (2006.01)
(Continued)

(52) U.S. Cl.
CPC ............. *A61M 21/02* (2013.01); *A61B 5/113* (2013.01); *A61B 7/006* (2013.01);
(Continued)

(58) Field of Classification Search
CPC .. A61M 21/00; A61M 21/02; A61M 21/0094; A61M 2012/0005; A61M 2012/0022; A61M 2012/0027; A61M 2012/0061; A61M 2012/0066; A61M 2012/0088; A61M 2021/0005; A61M 2021/0022; A61M 2021/0027; A61M 2021/0061; A61M 2021/0066;
(Continued)

(56) References Cited

U.S. PATENT DOCUMENTS 3,672,354 A  6/1972  Weber
3,809,065 A  5/1974  Gatts
(Continued)

FOREIGN PATENT DOCUMENTS

DE  43 12 542 A1  10/1993
DE  198 53 394 A1  5/2000
(Continued)

*Primary Examiner* — Charles A Marmor, II
*Assistant Examiner* — Thaddeus Cox
(74) *Attorney, Agent, or Firm* — Muncy, Geissler, Olds & Lowe, P.C.

(57) ABSTRACT

A device for generating sensory stimuli, corresponding to sensory stimuli emanating from a reference person, for a child comprises a receiving unit for receiving a data stream from a device for acquiring sensory stimuli, emanating from a reference person, and a transducer unit, which is coupled to the receiving unit and is controllable by the data stream. The transducer unit generates at least either body-borne sound, which corresponds to the heart sounds, described by the data stream, of the reference person, or movements, which correspond to the movements, described by the data stream, of the reference person, or airborne sound, which corresponds to the airborne sound generated by the reference person and is described by the data stream.

14 Claims, 6 Drawing Sheets

(51) Int. Cl.
*A61H 1/00* (2006.01)
*A61M 21/00* (2006.01)
*A61B 7/00* (2006.01)
*A61H 23/02* (2006.01)

(52) U.S. Cl.
CPC ...... *A61B 2562/0219* (2013.01); *A61H 1/001* (2013.01); *A61H 23/0236* (2013.01); *A61H 2203/0443* (2013.01); *A61H 2230/065* (2013.01); *A61M 2021/0016* (2013.01); *A61M 2021/0022* (2013.01); *A61M 2021/0027* (2013.01); *A61M 2021/0061* (2013.01); *A61M 2021/0066* (2013.01); *A61M 2021/0088* (2013.01); *A61M 2205/3375* (2013.01); *A61M 2205/3569* (2013.01); *A61M 2205/3592* (2013.01); *A61M 2230/06* (2013.01); *A61M 2230/205* (2013.01); *A61M 2230/30* (2013.01); *A61M 2230/50* (2013.01); *A61M 2240/00* (2013.01)

(58) Field of Classification Search
CPC ......... A61M 2021/0088; A61G 11/00–11/009; A61H 23/02; A61H 23/0236; A61H 2230/065; A61H 1/001
See application file for complete search history.

(56) References Cited

U.S. PATENT DOCUMENTS

| | | | |
|---|---|---|---|
| 4,066,072 A * | 1/1978 | Cummins | 601/15 |
| 4,863,461 A * | 9/1989 | Jarvik | 623/3.21 |
| 4,969,867 A * | 11/1990 | Cohen | A47G 9/0207 600/28 |
| 7,475,441 B1 | 1/2009 | Soberal | |
| 2005/0283039 A1* | 12/2005 | Cornel | 600/27 |
| 2007/0088410 A1 | 4/2007 | Chung et al. | |
| 2007/0179334 A1* | 8/2007 | Groves et al. | 600/28 |
| 2007/0262106 A1* | 11/2007 | Fidrych et al. | 224/264 |
| 2008/0092300 A1* | 4/2008 | Joe | A47D 13/08 5/655 |
| 2008/0097259 A1* | 4/2008 | Flick | A61G 7/05776 601/50 |
| 2010/0017967 A1* | 1/2010 | Murphy | A47C 31/001 5/698 |
| 2011/0144416 A1 | 6/2011 | Waddell | |
| 2013/0096368 A1* | 4/2013 | Devroey | 600/28 |

FOREIGN PATENT DOCUMENTS

| | | |
|---|---|---|
| DE | 101 23 893 A1 | 12/2002 |
| DE | 20 2007 008090 U1 | 8/2007 |
| GB | 2 331 887 A | 6/1999 |
| WO | WO 2011/063077 A1 | 5/2011 |

* cited by examiner

EMULATION OF SENSORY STIMULI, EMANATING FROM A REFERENCE PERSON, FOR A CHILD

This nonprovisional application claims priority under 35 U.S.C. §119(a) to European Patent Application No. 2 659 929, which was filed on May 3, 2013, and which is herein incorporated by reference.

BACKGROUND OF THE INVENTION

Field of the Invention

The present invention is directed to an emulation or simulation of sensory stimuli, emanating from a reference person, for a child spatially separated from the reference person. In particular, the present invention is directed to devices, a system, and a process for generating sensory stimuli, corresponding to the sensory stimuli emanating from a reference person, for a child.

Description of the Background Art

Birth represents a drastic change in all living conditions for a human. The direct physical contact of the newborn with his mother, to whose warmth, scent, voice, movements, and heartbeat it is already accustomed, is therefore especially important and valuable for it. This direct physical contact, however, is not always possible for medical and other reasons. Particularly after a premature birth, the newborn must often spend many weeks in an incubator.

For a newborn an incubator represents a hygienic chamber with an advantageous microclimate, particularly with an optimal temperature and humidity. The sensory stimuli familiar to the newborn from before its birth are absent, however, particularly the mother's movements, voice, heart sounds, and scent. There are numerous approaches to expose an infant or another person to suitable sensory stimuli.

U.S. Pat. No. 3,672,354 describes a device with an inflatable pad. An air compressor generates pressure pulses with the frequency of the human heartbeat.

U.S. Pat. No. 3,809,065 describes a system to expose a newborn to slowly changing environmental conditions. The temperature, tactile sensation, noises, movement, and light are slowly changed from conditions prevalent in the womb to those prevalent outside the womb.

U.S. Pat. No. 2011/0144416 A1 describes a device for generating rhythmic movements similar to those a child experiences on its mother's chest.

However, conventional devices, such as those described, impart to an infant only synthetic sensory stimuli that cannot replace the direct physical contact of the infant with its mother or its father. Conventional devices are often also mechanically complex in design, without creating from the infant's view an only approximately comparable substitute for the direct contact with the mother or father. Conventional devices often have only limited suitability for an incubator because they are not or not sufficiently transparent to x-rays.

Conventional devices are often not suitable for use in an incubator, because due to a low thermal conductivity of the employed materials and due to their design they have a negative effect on or interfere with the microclimate in the incubator and primarily the electrical thermal control system of the incubator. Conventional devices are often also mechanically complex in their design and therefore generate disturbing mechanical noises or vibrations, which produce a harmful acoustic environment, particularly a too high volume, for the infant in the incubator.

Conventional devices are often provided with large openings or open hollows or cavities or with connecting elements such as Velcro closures or zip fasteners. Because of the microclimate of the incubator, particularly the high humidity and temperature, water condensation can form on or in these and microorganisms can become established there. As a result, conventional devices can nullify the sterility of the incubator's interior and pose a high risk for premature children.

Conventional devices often have electrical components such as loudspeakers, motors, and other actuators, which are arranged especially directly beneath the infant's lying area. These electrical components represent a conceptual risk in the event of a possible electrical short circuit with the resulting heat generation and fire hazard and for this reason are not suitable or of only limited suitability for operation in the interior of an incubator.

Conventional devices are often also mechanically complex in design and have a variety of employed materials. In particular, conventional devices with integrated pneumatic or hydraulic cylinders or motors can contain lubricants and other harmful substances. Lubricants and other materials can be emitted as gases particularly in the humid and warm microclimate of the incubator and, for example, cause allergies in an infant or accumulate in blood and have an adverse health effect.

SUMMARY OF THE INVENTION

An object of the present invention is to provide improved devices, an improved system, and an improved process for generating sensory stimuli corresponding to sensory stimuli emanating from a reference person.

Embodiments of the present invention are based on the idea of acquiring by means of sensors the sensory stimuli produced by a parent (mother, father, stepmother or foster mother, stepfather or foster father) or another reference person, converting these to signals or a data stream, transmitting these to the child, and, under the control of the transmitted signals or the transmitted data stream, exposing the child to the corresponding sensory stimuli. The sensory stimuli to which the child is exposed are therefore not merely technical-synthetic in nature, are not merely recorded and reproduced, and are not standardized. Rather, the actual sensory stimuli from the mother (or the father or emanating from another reference person) are acquired, transmitted as a data stream, and simulated for the child. Thus, the child experiences the specific sensory stimuli, individual and characteristic with respect to their properties, which emanate from its active mother. The individual sensory stimuli characteristics, familiar to the child, are thereby retained in their variability and their time dependence properties. Therefore, a completely new quality of the simulation of the direct physical contact between the child and reference person, particularly between infant and mother, is created.

A device for generating sensory stimuli, corresponding to the sensory stimuli emanating from a reference person, for a child comprises a receiving unit for receiving a data stream from a device for acquiring sensory stimuli, emanating from a reference person, and a transducer unit, which is coupled to the receiving unit and is controllable by the data stream, for generating at least either body-borne sound, which corresponds to the heart sounds, described by the data stream, of the reference person, or movements, which correspond to the movements, described by the data stream, of the reference person, or airborne sound, which corresponds to the airborne sound generated by the reference person and is described by the data stream.

The reference person is especially the biological mother, the adoptive mother, stepmother, or foster mother, the biological father, the adoptive father, stepfather, or foster father. The reference person, however, can also be a (particularly much older) sibling or another reference person. The child is particularly an infant or a young child or a child of any age with a strong emotional relationship to a reference person, for example, a child whose mental and/or emotional development is retarded due to an illness or handicap.

The receiving unit is designed to receive a data stream provided by a device for acquiring and transmitting sensory stimuli emanating from a reference person. The receiving unit is therefore designed particularly for receiving a data stream generated and transmitted continuously in real time or with a slight time delay or with a constant time delay. The device differs essentially particularly from a device in which only recorded and stored sensory stimuli are reproduced.

The device may have one or more transducer units for generating body-borne sound and/or movements and/or airborne sound. Provided the transducer unit is designed to generate movements, it is designed in particular to generate movements corresponding to the chest movements, described by the data stream, of the reference person.

Body-borne sound is sound which propagates predominantly within a solid body or a liquid, especially within the body of the reference person or within an object on which the child lies. Airborne sound is sound that propagates predominantly in air. Without special measures, particularly without an at least extensive impedance matching, power transfer between body-borne sound and airborne sound often occurs only to a limited extent. Body-borne sound and airborne sound are normally perceived differently. Airborne sound is perceived via ear canals by the ears regardless of direct body contact; body-borne sound is perceived not only by the ears but perhaps also tactilely in direct or indirect body contact.

Airborne sound is created by a reference person particularly by means of his voice, by reading, singing, humming, clicking, whistling, etc. Body-borne sound is created by a reference person particularly in the form of heart sounds and sounds emanating from the digestive tract. The voice of the reference person as well is transmitted partially in the form of body-borne sound to a child, which has direct physical contact with the reference person.

In particular, two distinct and different transducer units for generating body-borne sound, on the one hand, and airborne sound, on the other, are provided according to the different sites and mechanisms of formation and according to the resulting different frequency spectra, amplitudes, and intensities.

In a device, as described here, the transducer unit comprises in particular at least either a sound generator for producing body-borne or airborne sound or a compressor or a pump for a fluid or a bladder or a motor for generating movements.

A loudspeaker is provided in particular as a sound generator for generating airborne sound. In particular a shuttle pump or a control bladder, which is provided with an electromechanical drive and is connected to a bladder at a lying area for the child, is provided as a sound generator for generating body-borne sound or as a transducer unit for generating vibrations. A ventilator or a fan is provided in particular as a compressor. The transducer unit can form a unit or a plurality of units, especially coupled together fluidically and/or by means of electrical or optical signal lines, for placement at a number of spaced-apart locations.

An electric motor, particularly a stepper motor, can be used as a motor for driving a control bladder, which is connected fluidically, for example, to a bladder for moving a lying area, or for the indirect driving of a lying area. An electric motor can be designed as a linear motor or as a rotating machine especially combined with a drive.

A device, as described here, further comprises in particular a lying area for a child.

In particular, the device comprises a mattress or a mat or some other pad whose top surface forms the lying area for the child. All other components of the device can be integrated into said mattress or mat or pad or be formed for a separate assembly. In particular, the mattresses or mats or pads are provided for an assembly within an incubator and other components of the device for an assembly outside the incubator.

In a device with a lying area, as it is described here, the transducer unit comprises in particular a bladder below the lying area and a control unit, whereby the control unit is connected fluidically to the bladder and comprises a pump or a compressor or a control bladder.

In particular two bladders are arranged symmetrically or substantially symmetrically next to one another beneath the lying area, like the lungs in a human being. One or more bladders filled with air or some other gas beneath the lying area can enable a uniform, extensive, low-noise, and low-vibration vertical movement of the lying area.

Alternatively or in addition, one bladder or a plurality of bladders can be provided and arranged to generate body-borne sound or vibrations, particularly corresponding to the heartbeat of the reference person, in or beneath the lying area. To generate body-borne sound, a bladder is filled in particular with a fluid.

In a device with a control unit, as it is described here, the control unit is spaced apart spatially particularly from the lying area and connected to the lying area by means of a fluid line.

The control unit comprises in particular one or more control bladders, pumps, compressors, or other devices for power transfer to a fluid and is provided and designed for an assembly outside an incubator. A fluid line for the fluidic coupling of the control unit to the bladder or bladders comprises in particular one or more pipes and/or one or more tubes.

A control unit spaced apart from the lying area can enable use of the device with a conventional incubator.

In a device, as described here, in particular the lying area and the bladder are designed for an assembly within an incubator and the control unit and the receiving unit for an assembly outside an incubator.

For an assembly within an incubator, the bladder and particularly the lying area are especially sterilizable or provided and designed as disposable products, whereas the control unit and the receiving unit because of their placement outside an incubator need not be sterilizable.

A device, as described here, also comprises particularly a hollow space for receiving an object serving as a scent source.

The hollow space is provided especially at the edge of the lying area. The hollow space is provided particularly for receiving a towel or some other object which has taken up the scent of the reference person and slowly releases it. The hollow space in particular has one or more openings through which a gas exchange occurs. The gas exchange can be supported by a ventilator or a fan. By placing an odor source in the hollow space, familiar environmental conditions can be created for the child also in regard to olfactory perception.

A device, as described here, comprises further in particular a sensor or a signal input for acquiring at least either sound produced by the child or movements of the child or a state of the child and for generating a further data stream, which describes the sound or the movements or the state, and a transmission unit for transmitting the further data stream to a receiving unit.

In particular a microphone for acquiring airborne or body-borne sound is provided as a sensor for acquiring sound. In particular, an analog or digital signal input for receiving data from one or more medical instruments is provided as a signal input. The state of the child comprises in particular its state of health, for example, its body temperature, its pulse rate, its blood pressure, its blood oxygen saturation, its respiratory rate, or parameters derived or calculated therefrom. The state of the child can comprise further parameters that describe its well-being or its sleeping or waking state. The transmission unit is provided in particular for transmitting the further data stream to a receiving unit on a reference person.

The last described features can enable a bidirectional interaction between the reference person and the child. In particular, the reactions of the child to sensory stimuli emanating from the reference person can be sent back to the reference person. Further, the reactions of the reference person to the sensory stimuli emanating from the child, to the child's state of health, or to utterances of the child can be transmitted from the reference person to the child. An interaction between the reference person and the child can thereby be enabled, which is similar to that in a direct physical contact. For example, the reference person can react to the child's health and, in turn, influence the child by movements, speaking, and even by purely autonomically controlled processes, for example, the heartbeat of the reference person.

In a device, as described here, the arrangement of the transducer unit or the transducer units relative to a provided arrangement and orientation of the child corresponds to the arrangement of the sources of the sensory stimuli on the reference person.

In particular, for example, a transducer unit for generating airborne sound or a loudspeaker is arranged at a head end of a lying area of the device, a transducer unit for generating body-borne sound is arranged in the middle of the lying area, and a transducer unit for generating vertical movements of the lying area is designed for a large-scale movement of the lying area. Thus, a child can receive the sensory stimuli in each case substantially from the direction from which it would have received them if it were lying, for example, on the chest of the reference person.

In a device, as described here, in particular a first transducer unit is designed for the data stream-controlled raising and lowering of a region of the lying area, which comprises at least one third of the lying area; a second transducer unit is designed for the data stream-controlled generation of body-borne sound or vibrations in the lying area and arranged in a middle region of the lying area; and a third transducer unit for the data stream-controlled generation of sound is arranged near an area provided for a child's head.

The first transducer unit is designed in particular for the data stream-controlled raising and lowering of a region of the lying area, which comprises at least half or at least two-thirds of the lying area or substantially the entire lying area.

A device, as described here, comprises in particular a light source for generating light and for exposing a child to the light.

The light can be provided for therapeutic purposes and have suitable properties for this (especially wavelength or intensity). The light source may be integrated especially into the described lying area in order to irradiate a child lying on the lying area. The light source can be designed to allow light with a substantially homogeneous light density or light with a substantially homogeneous intensity to emerge from the entire lying area or from a predefined region of the lying area. Alternatively, the light source can be designed to generate light or to allow it to emerge only in a region of the lying area in which a child lies on the lying area. To this end, the device can have in particular the properties and features, as they are described in U.S. Pat. No. 2007/0088410 A1.

In particular, a combination of one or more bladders, as they are described here, beneath the lying area with a light source is advantageous, because the bladder(s) can be transparent to the light of the light source. The light source can thus be arranged beneath the bladder(s). For this reason, the light source must not participate in the movement of the lying area and can be made and arranged fixedly.

A device for acquiring and transmitting sensory stimuli, emanating from a reference person, comprises a sensor at least either for acquiring the heart sounds of the reference person or for acquiring the chest movements of the reference person or for acquiring the airborne sound produced by the reference person, and for generating a data stream, which describes the heart sounds or the chest movements or the airborne sound, as well as a transmission unit for transmitting the data stream to a device for generating sensory stimuli, corresponding to the sensory stimuli emanating from the reference person, for a child.

The acquiring of heart sounds in particular does not mean only acquiring the pulse rate of the reference person. Rather, it includes body-borne sound and/or vibrations that can be produced by the reference person's heart activity in the reference person's chest and can be perceived by a child lying on the reference person's chest. The transmission unit is designed particularly for transmitting the data stream to a device for generating sensory stimuli, as they have been described above.

A device for acquiring and transmitting sensory stimuli, emanating from a reference person, comprises in particular further a receiving unit for receiving a further data stream and a transducer unit which is coupled to the receiving unit and is controllable by the further data stream, whereby the transducer unit is designed to generate at least either sound that corresponds to the sound produced by the child and described by the further data stream, or to generate movements that correspond to the child's movements described by the further data stream, or to display a child's state described by the data stream.

The child's state described by the data stream can be displayed graphically, particularly by means of symbols, alphanumerically, optically, acoustically, haptically, and/or in some other manner. This can enable feedback from the child to the reference person and thereby a bidirectional interaction between the reference person and child.

A device for acquiring and transmitting sensory stimuli emanating from a reference person is especially designed to be worn on the chest by a reference person.

The device is designed in particular with respect to its spatial-geometric configuration, its weight, and with respect to its surface properties to be carried like an infant on the chest and, in so doing, to be perceived in a manner reminiscent of an infant.

A device for acquiring and transmitting sensory stimuli emanating from a reference person, as it is described here, has in particular a carrying strap or a fastening means for a carrying strap.

A system comprises in particular a device for generating sensory stimuli, as it is described here, and a device for acquiring and transmitting sensory stimuli emanating from a reference person, as it is described here.

The devices described here and the system described here are designed in particular to exchange the data stream and optionally also the further data stream in an analog and/or digital manner and in the form of electrical, optical, electromagnetic, acoustic, and other signals. A transmission channel between both devices can comprise an electrical and/or optical point-to-point connection, an electrical or optical bus, the Internet, a telephone network, or some other private or public network and comprise technologies such as WLAN, WiFi, GSM, UMTS, and/or other technologies. Particularly in a bidirectional data exchange, in which both a data stream is transmitted from the reference person to the child and also a further data stream from the child to the reference person, the transmission occurs in particular in real time or with the shortest possible delay amounting to a few seconds or less.

In a process for generating sensory stimuli, corresponding to sensory stimuli emanating from a reference person, for a child spatially separated from the reference person, at least either heart sounds of the reference person or movements of the reference person or airborne sound generated by the reference person are acquired; a data stream, describing the heart sounds or the movements or the airborne sound, is generated; the data stream is transmitted from the reference person to the child; and body-borne sound, corresponding to the heart sounds and controlled by the data stream, or movements corresponding to the movements or airborne sound corresponding to the airborne sound are generated.

The data stream is transmitted particularly from a transmission unit or transmitter on a device worn by the reference person to a receiving unit of a device for the child. The acquired movements are in particular the movements of the reference person's chest.

In a process, as described here, particularly also at least either sound produced by a child or the movements of the child or a state of the child is acquired; a further data stream which describes the sound or the movements or the state is generated; the further data stream is transmitted from the child to the reference person; and sound or movements or a signal perceivable by the reference person are generated at the reference person by the further data stream.

The data stream is transmitted particularly from a transmission unit of a device at the child to a receiving unit of a device arranged on the reference person. The conversion of the data stream into a signal perceivable by the reference person comprises in particular the generation of a graphical, alphanumeric, acoustic, optical, or some other display of the child's state.

A process, as described here, can be carried out particularly with devices, as they are described here.

A device for generating sensory stimuli for a child comprises a body made of an elastic material, a lying area for a child on the body, and a bladder for generating a vertical movement of the lying area, whereby the bladder is embedded in the elastic material of the body.

The body with the lying area and bladder forms in particular a mattress for placement in an incubator. The bladder or a plurality of bladders is designed in particular for creating in the body a vertical movement that corresponds to a movement, caused by breathing, of the front side of the upper body of the mother or another adult person, and/or for producing body-borne sound that corresponds to the heartbeat of a mother or some other adult person. The body-borne sound manifests itself particularly in the vertical movements of the lying area, which can differ from movements, corresponding to breathing movements, in frequency, amplitude, spatial distribution, and time dependence.

The elastic material of the body has in particular a mass density that is similar to that of the human body or muscle or fatty tissue of the human body. The elastic material of the body has in particular a high thermal conductivity in order to enable a uniform temperature control of the body, for example, in an incubator. The elastic material of the body comprises in particular polyurethane rubber, polyurethane gel, latex, or another elastic material.

In a device with a body made of an elastic material, as it is described here, the body has in particular no further hollow spaces apart from the bladder or a plurality of bladders.

Because the body has no further hollow spaces, soiling of hollow spaces and colonization of hollow spaces by microorganisms are ruled out. For this reason, the device can be especially easy to clean and to sterilize.

A device with a body made of an elastic material, as it is described here, is produced particularly by a casting process, in which the elastic material of the body is connected by material bonding with the elastic film and with the bladder over the entire surface or substantially over the entire surface.

In this case, in particular no hollow spaces are produced. The elastic material, the elastic film, and the bladder therefore form a monolithic unit, also inseparable after elastic deformation repeated over a long time period, which has only outer surfaces, which can be easily cleaned and sterilized, apart from the inner surfaces of the bladder or bladders.

A device with a body made of an elastic material, as it is described here, comprises in particular further an elastic film on the surface of the body, which forms at least the lying area.

The elastic film has in particular polyurethane or polycarbonate or a similar elastic material. The elastic film is so elastic that, together with the body, it can be readily deformed elastically by the bladder or bladders.

The elastic film has in particular a closed or pore-free or low-pore and easily wipable surface. In particular, the elastic film is gas-tight. The elastic film may have bacteriostatic, bactericidal, virustatic, virucidal, and/or other germicidal properties. The elastic film can cover the entire surface of the body. The elastic film can simplify the cleaning and/or sterilization of the device.

A device with a body made of an elastic material, as it is described here, comprises in particular a first bladder and a second bladder, which are embedded in the body, whereby the arrangement of the first bladder and the second bladder in the body corresponds substantially to the arrangement and expansion of the area, moved by breathing, and the heart in the body of a mother.

Because of the elasticity of the human body, the area, moved by breathing, of a mother's body is greater than the area taken up by the lungs and extends into the abdominal area particularly because of the movement of the diaphragm.

By the described arrangement of the bladders a movement of the lying area can be produced which corresponds in good approximation to the movement of the front side of the upper body of a mother or of another adult person by breathing and/or beating of the heart. The topology of the front side of the upper body of a mother or another adult person can be simulated by the design, particularly the form or configuration, of the lying area and an edge region at or around the lying area. Both of these can serve to offer a child, particularly a newborn, an environment that resembles that on the front side of the upper body of the recumbent mother.

The first bladder is particularly made as two parts or as a pair. Stated differently, two first bladders in particular are arranged symmetrically in the body in order to simulate the lungs of the human body.

In a device with a body made of an elastic material, as it is described here, particularly the material of the body and optionally the material of the film and optionally the material of the bladder(s) are transparent to x-rays.

In particular, the materials of the indicated components of the device have no metals or other elements with a higher atomic number, which absorb or scatter x-rays. This can enable the x-raying of a child lying on the lying area of the device through the body.

In a device with a body made of an elastic material, as it is described here, particularly the material of the body and optionally the material of the film and optionally the material of the bladder(s) are transparent or translucent to visible light and/or ultraviolet light.

A transparent or translucent design of the device can enable phototherapy of a child, lying on the lying area of the device, also from the bottom side.

A device with a body made of an elastic material, as it is described here, is provided and designed particularly for use in a system, as described here, or for a combination with a device for acquiring and transmitting sensory stimuli emanating from a reference person. A system comprises in particular a device with a body made of an elastic material, as it is described here, and a device for acquiring and transmitting sensory stimuli emanating from a reference person.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
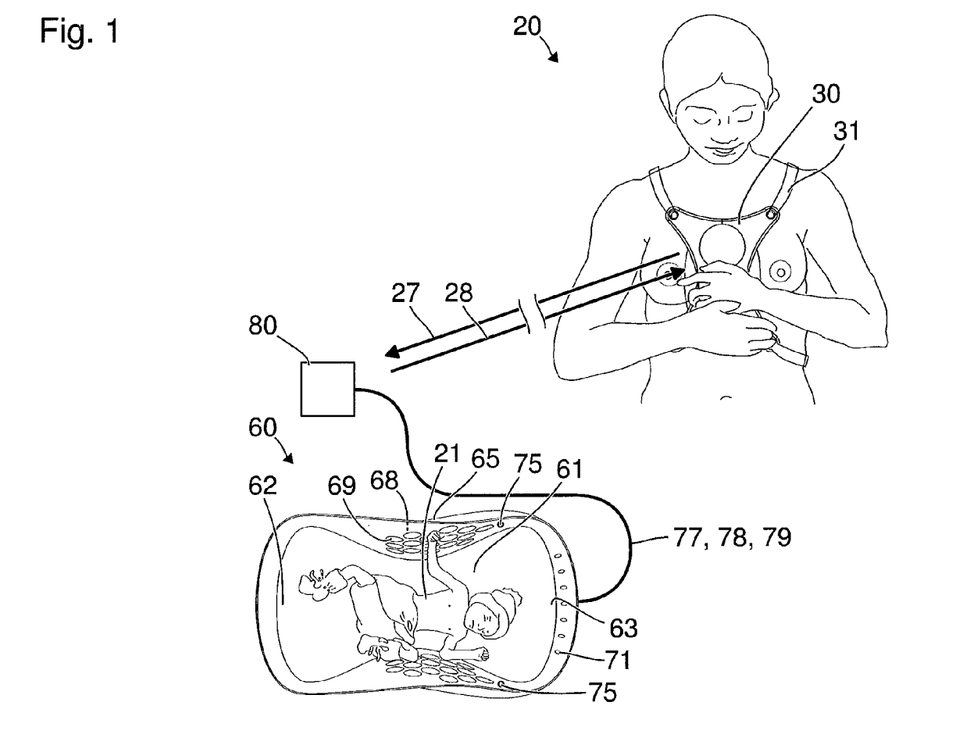
FIG. 1 a schematic illustration of a system.

FIG. 1 shows a schematic illustration of a system for transmitting sensory stimuli between a mother 20 and an infant 21 spatially separated from the mother. Mother 20 wears a sensor unit 30 in a position similar to how she could carry infant 21, if there were, for example, no medical reasons against this. Sensor unit 30 is attached to the mother 20 by means of a carrying strap 31. The features of sensor unit 30 will be described in greater detail below with reference to FIGS. 5 to 8.

The infant 21 lies on a mattress 60, which can be placed in an incubator. Mattress 60 has a lying area 61 with a foot end 62, a head end 63, and long sides 65. A hollow space 68 with a plurality of openings 69 are provided on both of the opposite long sides 65 of lying area 61. At head end 63 of lying area 61, one or more loudspeakers 71 are provided, particularly behind the corresponding openings in the surface of mattress 60. One or more microphones 75 are provided in the vicinity of head end 63 of lying area 61. A microphone 75 is arranged particularly at each long side 65 near head end 63 of mattress 60 and near the head of infant 21. Features and properties of mattress 60 will be described in greater detail below with reference to FIGS. 2 to 4.

Mattress 60 is connected to a control unit 80 via signal and fluid lines 77, 78, 79, which are combined into a bundle. Control unit 80 will be described in greater detail below with reference to FIG. 9. A first data stream 27 is transmitted from sensor unit 30 to control unit 80. A second data stream 28 is transmitted from control unit 80 to sensor unit 30.

Figure 2:
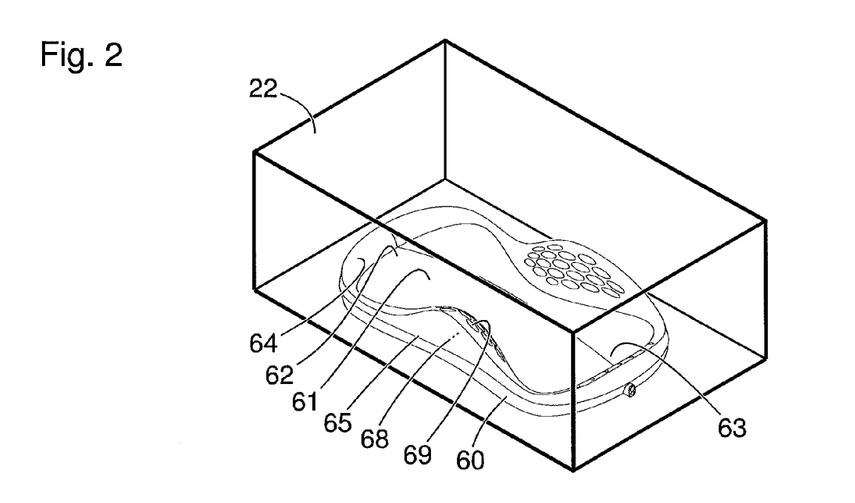
FIG. 2 a schematic axonometric illustration of an incubator with a device for generating sensory stimuli.

FIG. 2 shows a schematic axonometric illustration of mattress 60 in an incubator 22 indicated as a simple transparent cuboid. It is evident in the axonometric illustration of FIG. 2 that a circumferential edge region 64, limiting lying area 61, of mattress 60 is configured raised. Hollow spaces 68 are formed in the middle areas of long side 65 under edge region 64. To this end, edge region 64 is made bulging upward in the middle of long side 65 and toward lying area 61.

Figure 3:
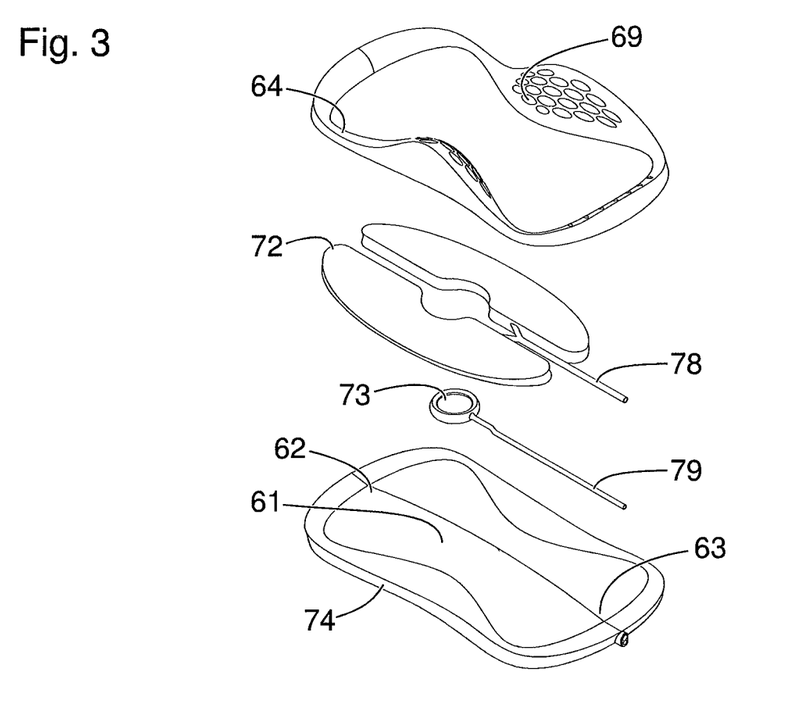
FIG. 3 a schematic exploded view of the device for generating sensory stimuli.

FIG. 3 shows a further schematic axonometric illustration of mattress 60, whereby components of mattress 60 are shifted vertically relative to one another in the manner of an exploded illustration. Mattress 60 comprises a pair of substantially symmetrically formed and arranged first bladders 72 and a second bladder 73 in a hollow base element 74, which forms the top side of lying area 61.

First bladders 72 are connected to a first fluid line 78. Second bladder 73 is connected to a second fluid line 79.

First bladders 72 take up a large part of the surface of base element 74 and a large part of lying surface 61. By supplying and removing air, another gas, or a liquid to or from first bladders 72, large areas of lying area 61 can be moved vertically or raised and lowered. By supplying and removing air or another fluid by second fluid line to or from second bladder 73, lying area 61 can also be raised or lowered but on a smaller scale. First bladders 72 are provided and designed for low-frequency raising and lowering of lying area 61 according to the chest breathing movements of mother 20. Second bladder 73 is provided and designed for generating body-borne sound or vibrations in lying area 61, particularly according to the heart sounds of mother 20.

Figure 4:
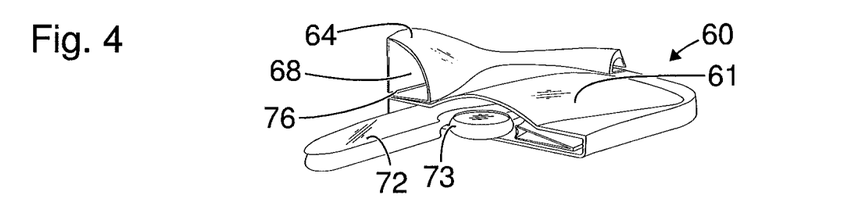
FIG. 4 a further schematic illustration of the device of FIGS. 2 and 3.

FIG. 4 shows a further schematic axonometric illustration of mattress 60. Mattress 60 is shown partially cut open in order to make the structural features visible.

In the example shown here, the base element is formed as a single piece and forms a pocket in which first bladders 72 and second bladder 73 are arranged. The top side of base element 74 forms lying area 61. Edge region 64 of the lying area is configured as a separate part, only loosely placed or, glued to the rest of mattress 60 or joined to it in some other manner. Hollow space 68 is accessible through an outer circumferential slit 76.

Figure 5:
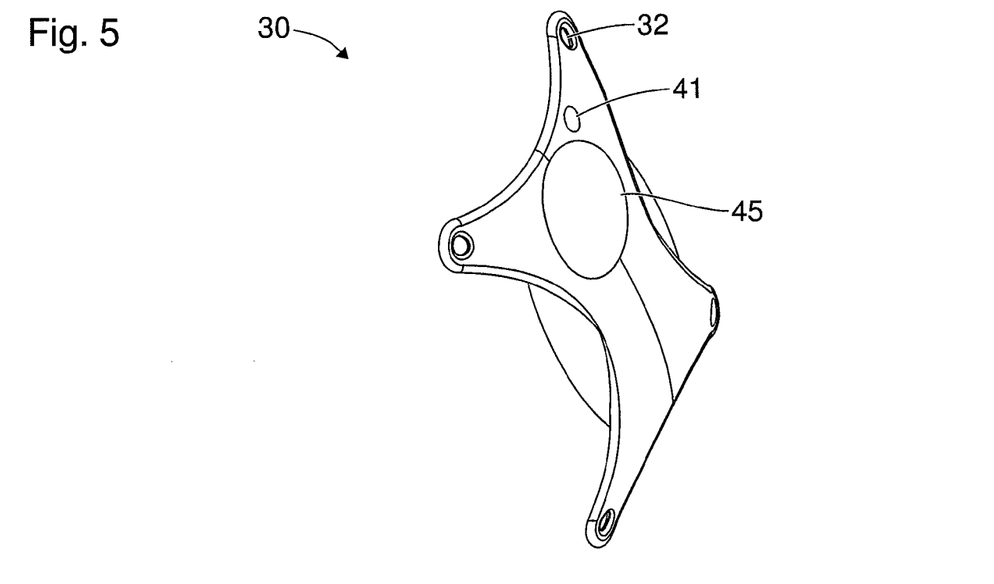
FIG. 5 a schematic axonometric illustration of a device for acquiring sensory stimuli.

FIG. 5 shows a schematic axonometric illustration of sensor unit 30 of FIG. 1. Sensor unit 30 has fastening means 32, formed as eyelets, for carrying strap 31 (cf. FIG. 1). Sensor unit 30 has a first microphone 41 and a display device 45 on the surface, which in FIG. 5 is shown partially facing the viewer and is provided for an arrangement facing away from mother 20.

Display device 45 is designed to show the operating state of sensor unit 30 and/or information contained in second data stream 28 (cf. FIG. 1) about infant 21 by symbols, pictograms, or in another graphical manner, alphanumerically, acoustically, and/or by means of light signals. The information about infant 21 to be displayed includes in particular its state of health, its waking or sleeping state, its pulse rate, its blood pressure, its blood oxygen saturation, and other parameters. Further, sensor unit 30 can be designed to reproduce by means of a loudspeaker sounds produced by infant 21 and transmitted by means of second data stream 28.

Figure 6:
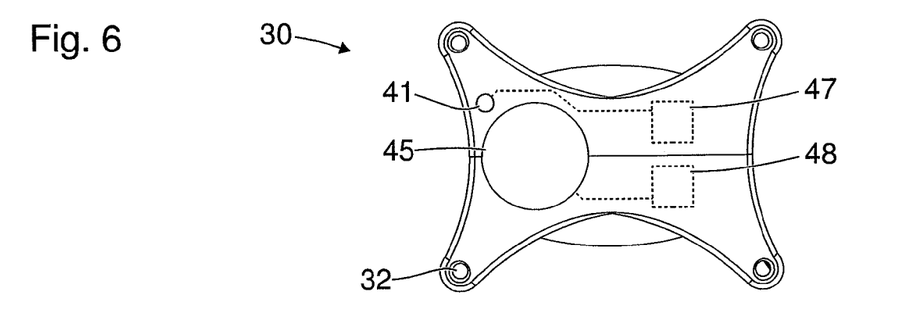
FIG. 6 a further schematic illustration of the device of FIG. 5.
Figure 7:
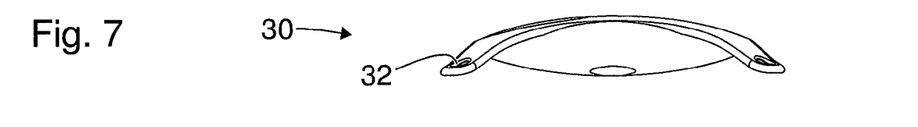
FIG. 7 a further schematic illustration of the devices of FIGS. 5 and 6.
Figure 8:
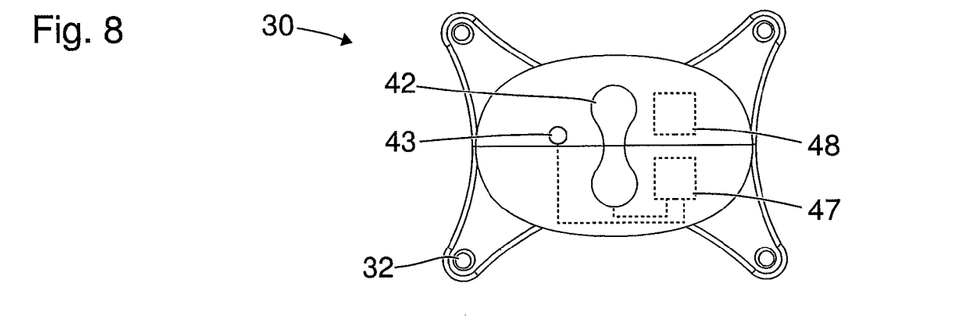
FIG. 8 a further schematic illustration of the device of FIGS. 5 to 7.

FIGS. 6 to 8 show further schematic illustrations of the sensor unit of FIGS. 1 and 5. In FIG. 6, the side facing away from the mother during the intended use of sensor unit 30 is shown. In FIG. 8, the side facing the mother during the intended use of sensor unit 30 is shown. In FIG. 7, sensor unit 30 is shown from the side; the plane of the drawing in FIG. 7 is therefore perpendicular to the planes of the drawing in FIGS. 6 and 8.

In FIG. 8, a sensor 42 for acquiring the chest movements of the mother and a microphone 43 for acquiring the mother's heart sounds are provided on the side facing the mother. Sensor 42 and second microphone 43 in particular are provided and designed to lie directly against the mother's skin. The sensor for acquiring chest movements can be designed as an acceleration sensor and in this case be placed in the interior of sensor unit 30. Further, the sensor for acquiring chest movements in the form of a force sensor can be integrated in fastening means 32 for a carrying strap 31 (cf. FIG. 1) or in a carrying strap 31.

A transmission unit or a transmitter 47 and a receiving unit or a receiver 48 are placed in the interior of sensor unit 30; these are not visible and for this reason indicated only by dashed lines in FIGS. 6 and 8. First microphone 41, sensor 42, and second microphone 43 are connected to transmitter 47 by signal lines indicated by the dashed lines. Display device 45 is connected to receiver 48 by a signal line indicated by dashed lines.

Transmitter 47 and receiver 48 can each have a data processing device, for example, for analog-to-digital conversion, for digital-to-analog conversion, for data compression, or for data decompression. Alternatively or in addition, first microphone 41, sensor 42, second microphone 43, and display device 45 can each have a data processing device, particularly for data compression, for data decompression, for analog-to-digital conversion, or for digital-to-analog conversion. As a departure from the illustration in FIGS. 6 and 8, first microphone 41, sensor 42, second microphone 43, display device 45, transmitter 47, and receiver 48 can be partially or fully integrated. Further, as a departure from the illustration in FIGS. 6 and 8, a separate data processing device can be provided, which is connected by signal lines to first microphone 41, sensor 42, second microphone 43, display device 45, transmitter 47, and receiver 48.

It is evident in the overview of FIGS. 1 and 5 to 8 that sensor unit 30 has a form or configuration which, on the one hand, corresponds to ergonomic requirements and, on the other, resembles the shape of an infant's torso. In particular, sensor unit 30 on the side facing the mother has large radii of curvature and a soft surface.

Sensor unit 30 is a device for acquiring and transmitting sensory stimuli produced by or emanating from the mother 20 or another reference person. Departing from the properties of sensor unit 30 shown here, such a device may have a plurality of separate components. These components are coupled to one another particularly by cables or some other signal line (particularly in compliance with Bluetooth or another wireless standard). For example, sensors, whose signals are transmitted in analog or digital form to a separate data processing unit, are arranged in one or more units on the chest. The separate data processing unit can be worn, for example, on the belt or in a pocket and can comprise communication means for transmitting the first data stream via WLAN, WiFi, GSM, UMTS, or in some other manner.

Figure 9:
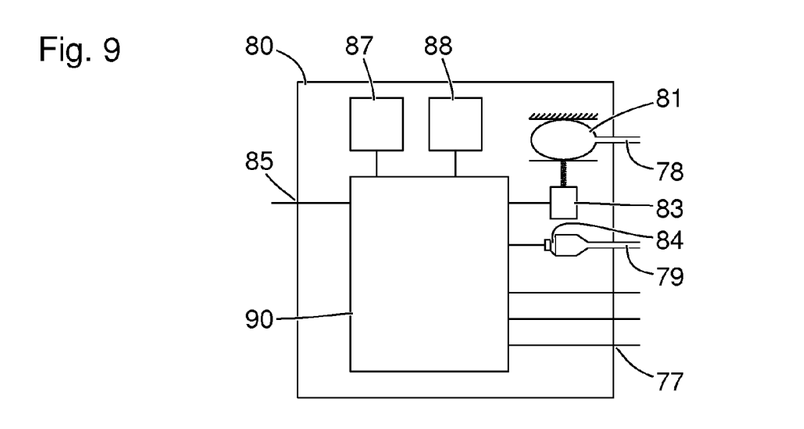
FIG. 9 a schematic illustration of a control unit.

FIG. 9 shows a schematic illustration of control unit 80 of FIG. 1. Control unit 80 comprises a control bladder 81, which is connected by means of first fluid line 78 to first bladders 72 beneath lying area 61 (cf. FIGS. 3 and 4). The volume of first control bladder 81 is alterable by an associated drive 83. Drive 83 comprises, for example, a stepper motor or some other electric motor and a threaded spindle or some other drive.

Further, control unit 80 comprises a device 84, which is coupled fluidically to the second bladder 73 by means of second fluid line 79 (cf. FIGS. 3 and 4). Device 84 comprises, for example, a membrane driven by an electromagnet, by means of which a volume can be varied and which can be connected to the second bladder 73 by means of second fluid line 79. The membrane and the electromagnet can be part of a conventional loudspeaker or be arranged in the manner of a conventional loudspeaker. Alternatively, device 84 is a shuttle pump or some other device for the controlled variation of pressure in a fluid.

Further, control unit 80 comprises a receiving unit or a receiver 87 for first data stream 27 (cf. FIG. 1) and a transmission unit or a transmitter 88 for second data stream 28. As a departure from the illustration in FIG. 9, receiver 87 and transmitter 88 can be integrated partially or fully into the same component. Transmitter 47 and receiver 48 are each designed for transmitting or receiving electrical signals via one or more electrical lines, electromagnetic signals by means of one or more antennas, and/or (visible or UV) light signals by means of light sources or light sensors. Transmitter 47 and receiver 48 comply with, for example, an industry standard, for example, Bluetooth, WLAN, GSM, UMTS or 3G DECT.

Further, control unit 80 comprises a data processing device 90. Data processing device 90 can contain one or more processors and/or controllers, volatile and non-volatile memories, and other components. Data processing device 90 is effectively connected to drive 83 for control bladder 81, device 84, receiver 87, and transmitter 88. Further, data processing device 90 is connected to microphone 75 and loudspeaker 71 (cf. FIG. 1) by means of signal lines 77.

Figure 10:
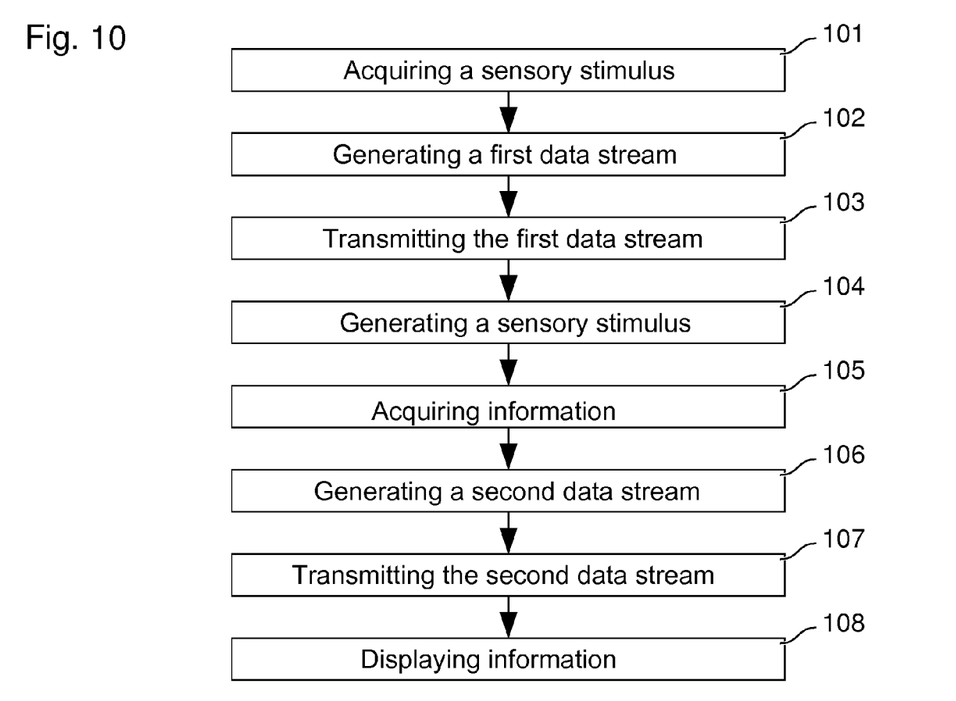
FIG. 10 a schematic flowchart.

FIG. 10 shows a schematic flowchart of a process for generating sensory stimuli, corresponding to sensory stimuli emanating from a reference person, for an infant spatially separated from the reference person or another child spatially separated from the reference person. The process is especially executable with a system and devices with the properties and features, as they have been presented above with use of FIGS. 1 to 9. However, the process can also be executed with a system and devices that have features and properties different from the features and properties presented above with use of FIGS. 1 to 9. Nonetheless, to simplify understanding, reference will be made below by way of example to the system and devices presented above with use of FIGS. 1 to 9.

In a first step 101, by means of a microphone 43 on a sensor unit 30 worn by a reference person, heart sounds of the reference person or other sounds produced by the reference person 20 and sounds or vibrations propagating within the torso of reference person 20 are acquired substantially in the form of body-borne sounds. Alternatively or in addition, in first step 101 movements of the chest of reference person 20 (particularly breathing movements) or other movements of reference person 20 can be acquired by means of a sensor 42 on sensor unit 30. Alternatively or in addition, in first step 101 an airborne sound generated by reference person 20 can be acquired by means of a microphone 41, especially spoken or sung sounds. Alternatively or in addition, in first step 101 the body temperature of reference person 20 can be acquired. Alternatively or in addition, in first step 101 inputs of reference person 20 on a keyboard or some other user interface can be acquired. All parameters and data acquired in first step 101 may originally be present particularly in the form of analog electrical signals, which can then be digitalized before or in the second step described next.

A first data stream 27 is generated in a second step 102. First data stream 27 is especially a continuously generated data stream, which contains or describes several or all parameters, acquired in first step 101, in analog or digital form. A selection or manipulation of data occurs in the second step. In particular, data can be filtered, suppressed or hidden, or replaced. For example, reference person 20 has the opportunity to turn off a microphone by means of a button or a switch on sensor unit 30 or to reduce the sensitivity of a microphone, if the reference person is in a loud environment or exposed to unpleasant noises.

In a third step 103, first data stream 27 is transmitted from sensor unit 30, particularly from transmitter 47 of sensor unit 30, to a spatially distant control unit 80, particularly to a receiver 87 of control unit 80. The transmission of the first data stream can occur in the form of electrical, electromagnetic, acoustic, or other signals. In this regard, first data stream 27 is transmitted particularly by a transmitting device or a transmitter 47 of sensor unit 30 and received by a receiving unit or a receiver 87 of control unit 80.

In a fourth step 104, sensory stimuli, which correspond or substantially correspond to the sensory stimuli acquired in first step 101, for a child 21 are generated controlled by first data stream 27 of control unit 80 and a mattress 60. In particular, a drive 83 for a control bladder 81 is controlled by a data processing device 90 of control unit 80 and the volume of control bladder 81 is thereby varied, whereby because of the fluidic coupling of control bladder 81 to first bladders 72, a lying area 61 of a mattress 60 is raised and lowered according to the breathing movements, acquired in first step 101, of reference person 20. Alternatively or in addition, in fourth step 104, body-borne sound or a vibration, which corresponds in particular to the heart sounds generated by reference person 20 and acquired in first step 101, is produced in lying area 71 by means of a device 84 of control unit 80, a second fluid line 79, and a second bladder 73, which is coupled mechanically to lying surface 61. Alternatively or in addition, in fourth step 104 airborne sound, which corresponds to the airborne sound produced by reference person 20 and acquired in first step 101 by means of microphone 41, is produced by one or more loudspeakers 71.

In a fifth step 105, at least either sound, produced by child 21, or a movement of child 21 is acquired. Sound produced by child 21 is acquired in particular by one or more microphones 75 on mattress 60. The child's movements can be acquired optically, by means of strain gauges or by other force sensors or by means of acceleration sensors. Further, in fifth step 105 alternatively or in addition, the body temperature, pulse rate, blood pressure, blood oxygen content, and/or other parameters, describing or characterizing the state of health and/or sleeping or waking state of child 21, can be acquired. These parameters can be acquired by sensors, which are part of the system described here, particularly of mattress 60. Alternatively, the parameters of other medical instruments can be received, especially via a signal input 85 on control unit 80.

In a sixth step 106, a second data stream 28 is generated, which describes the sound, acquired in fifth step 105 and/or the child's movement, acquired in fifth step 105, and/or other parameters and information acquired in fifth step 105. Second data stream 28 can describe the sound and/or the movement and optionally the further parameter(s) and information in an analog or digital manner. The sixth step 106 is carried out in particular by control unit 80, for example, by a data processing device 90 of control unit 80.

In a seventh step 107, second data stream 28 is transmitted from control unit 80 to sensor unit 30. This occurs in the form of electrical, electromagnetic, light, acoustic, or other signals. In this regard, second data stream 28 is transmitted in particular by a transmitting unit or a transmitter 88 of control unit 80 and received by a receiving unit or a receiver 48 of sensor unit 30.

In an eighth step 108, second data stream 28 is converted to sound, described by second data stream 28, and/or into movement, described by second data stream 28. Alternatively or in addition, in eighth step 108 a state of child 21, described by second data stream 28, is displayed in the form of symbols or pictograms or in some other graphical, alphanumeric, or acoustic manner or by means of light signs. Eighth step 108 is carried out in particular by display device 45 on sensor unit 30.

All steps are carried out especially continuously or quasi-continuously and thereby substantially simultaneously. In particular, fifth step 105, sixth step 106, seventh step 107, and eighth step 108 are optional.

Figure 11:
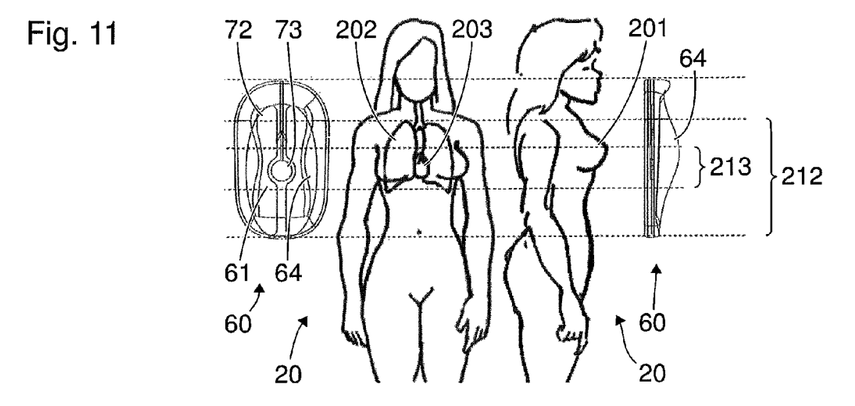
FIG. 11 a schematic comparison of a mother with a device for generating sensory stimuli.

FIG. 11 shows a schematic comparison of a mother 20 with a mattress 60, as it is illustrated above with use of FIGS. 1 to 4. Mother 20 of a younger childbearing age with an average height and average build and mattress 60 are shown approximately in the same scale. In FIG. 11, mother 20 is illustrated twice in the center, namely frontally on the left and from the side on the right. Mattress 60 is shown twice, namely in a plan view on the left and in a side view on the right.

In the frontal view of mother 20, the positions and expansions of lungs 202 and heart 203 are indicated. In the plan view of mattress 60, first bladder 72 for generating vertical movements (perpendicular to the plane of the drawing in FIG. 11) of lying area 61 of mattress 60 and second bladder 73 for generating body-borne sound, which corresponds in particular to the human heartbeat, are indicated in mattress 60.

Area 212, moved by breathing, of the upper body of mother 20 and area 213, in which heart 203 of mother 20 is located, are indicated by horizontal dashed lines in FIG. 11. Area 212, moved by breathing, of the upper body of mother 20 is somewhat larger than the area taken up by lungs 202 and extends into the abdominal area of mother 20, because the abdominal area and the organs located therein are also moved during breathing by the movement of the diaphragm.

In the comparison of mother 20 and mattress 60, as shown in FIG. 11, it is evident that the expansion of first bladders 72 in mattress 60 corresponds substantially to area 212, moved by breathing, of the upper body of mother 20 and the area within which second bladder 73 is located substantially to area 213 in which heart 203 of mother 20 is located. It can be seen further that circumferential edge region 64 of mattress 60 is raised and expanded in a middle side region approximately corresponding to breasts 201 of mother 20.

The topology of the front side of the upper body of mother 20 and of the movement thereof by breathing and beating of the heart are therefore simulated by the arrangement and configuration of first bladders 72 and second bladder 73 in mattress 60, the form or configuration of lying surface 61, and the form or configuration of circumferential edge region 64 of mattress 60.

Figure 12:
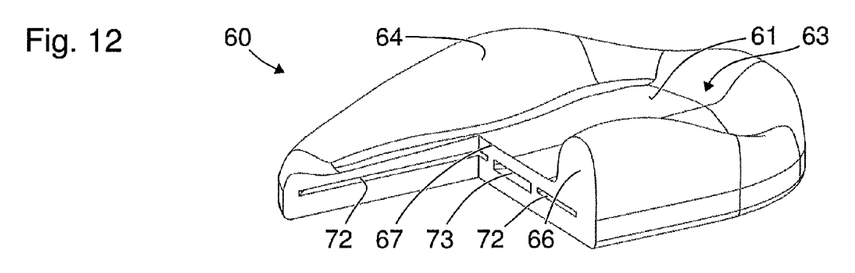
FIG. 12 a schematic axonometric sectional illustration of a further device for generating sensory stimuli.

FIG. 12 shows a schematic axonometric sectional illustration of a further mattress 60, which is designed as a device for generating sensory stimuli for a child and which simulates the mattress shown above with use of FIGS. 1 to 4 and 11 in some features and properties, particularly in the form or configuration of lying surface 61 and circumferential edge region 64 of mattresses 60. Only the features and properties will be described hereafter in which mattress 60 differs from the mattresses shown above with use of FIGS. 1 to 4 and 11. Mattress 60 is shown by two sections cut open in two vertical half-planes, orthogonal to one another, in order to show the internal structure of mattress 60.

Mattress 60 differs from the mattresses shown above with use of FIGS. 1 to 4 and 11 particularly in that bladders 72, 73 are not arranged in a hollow space beneath the lying surface but in a body 66 made of an elastic material. Body 66 is made of a polyurethane rubber, polyurethane gel, latex, or another elastic material. The elastic material of body 66 has in particular a similar mass density and a similar elasticity as human muscle or fatty tissue. The elastic material of body 66 has in particular as high a thermal conductivity as possible in order to enable uniform temperature control within an incubator 22 (cf. FIG. 2).

An elastic film 67, which forms in particular lying surface 61 of mattress 60, is provided on the surface of body 66. Elastic film 67 can completely cover body 66 or the surface thereof. Alternatively, for example, the bottom side of mattress 60, said side facing away from lying area 61, is covered by a stiffer film or a film of lower elasticity. Film 67 has in particular a smooth, wipable, closed surface, which simplifies cleaning and sterilization of mattress 60. In particular, elastic film 67 is designed to have a low permeability for microorganisms.

Bladders 72, 73 are surrounded especially completely and directly by the elastic material of body 66. Except for bladders 72, 73, mattress 60 within the spatial region enclosed by film 67 has no other hollow spaces or openings which microorganisms could colonize.

The elastic material of body 66, the material of elastic film 67, and optionally the materials of elastic films forming the surface of bladders 72, 73, are particularly transparent to x-rays, in order to enable x-raying of a child on lying area 61 through mattress 60. To this end, the elastic material of body 66, the material of elastic film 67, and optionally the materials of films forming the surface of bladders 72, 73, have in particular exclusively light elements or elements with a lower atomic number, which do not absorb or scatter x-rays or absorb or scatter them to a low extent.

The elastic material of body 66, the material of elastic film 67, and optionally the materials of elastic films, forming the surface of bladders 72, 73, are transparent or translucent especially to visible light and/or ultraviolet light, in order to enable a phototherapy for a child, lying on lying area 61 of mattress 60, from the bottom side as well.

Figure 13:
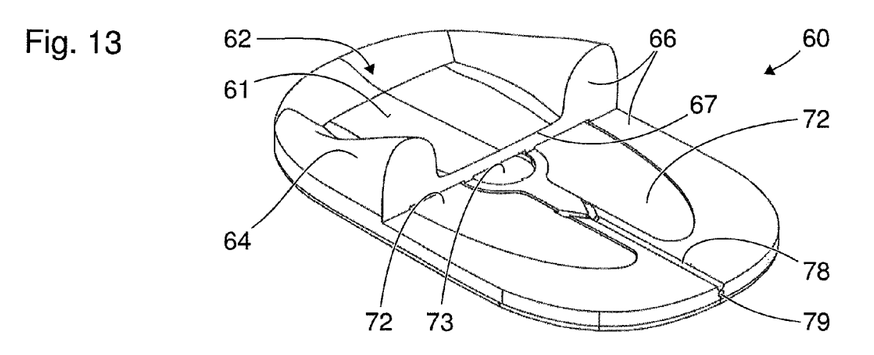
FIG. 13 a further schematic axonometric sectional illustration of the device of FIG. 12.

FIG. 13 shows a further schematic axonometric sectional illustration of mattress 60 of FIG. 12. The illustration in FIG. 13 differs from the illustration in FIG. 12 in that the mattress is cut open along a horizontal half-plane and a vertical half-plane. Because of the location of the horizontal section, the shape of bladders 72, 73 can be seen which correspond to those of the mattress shown above with use of FIGS. 1 to 4 and 11. Further, fluid lines 78, 78, embedded in the elastic material of body 66, for a fluidic control of bladders 72, 73 are also visible.

Figure 14:
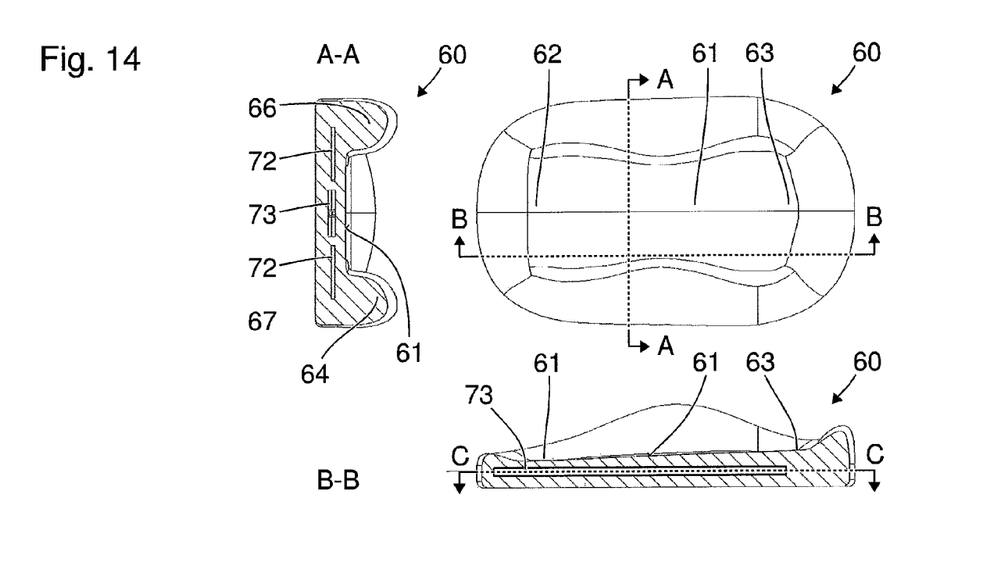
FIG. 14 a schematic plan view and two schematic sectional illustrations of the device of FIGS. 12 and 13.

FIG. 14 shows a schematic plan view at the top on the right, and at the bottom and on the left two schematic sectional illustrations of mattress 60, illustrated above with use of FIGS. 12 and 13. The plane of the drawing in the plan view on the right at the top is horizontal in FIG. 14. Sectional plane A-A of the section shown on the left in FIG. 14 and sectional plane B-B of the section shown at the bottom in FIG. 14 are indicated in the plan view shown at the top on the right in FIG. 14. Sectional plane A-A is selected such that it cuts through not only first bladders 72 but also second bladder 73. Sectional plane B-B is selected so that it cuts only one of first bladders 72.

Figure 15:
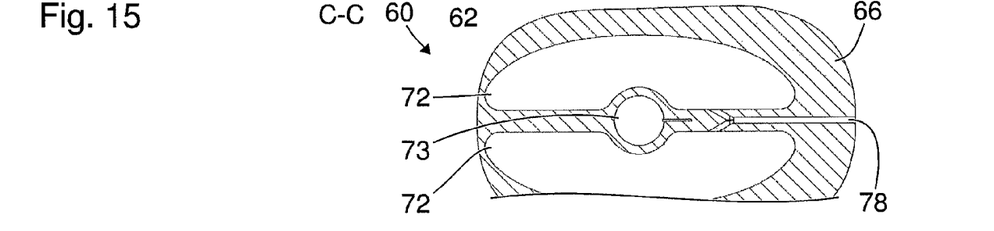
FIG. 15 a further schematic sectional illustration of the device of FIGS. 12 to 14.

FIG. 15 shows a further schematic sectional illustration of mattress 60 illustrated above using FIGS. 12 to 14. Horizontal sectional plane C-C of FIG. 15 is indicated in the section shown at the bottom in FIG. 14 along plane B-B. Sectional plane C-C of FIG. 15 runs within bladders 72, 73. Because mattress 14 is designed mirror symmetric, only one half is shown completely and the other incompletely.

It is evident in FIGS. 12 and 14 that bladders 72, 73 each have flat cross sections. In FIGS. 13 and 15, the extension of bladders 72, 73 in the horizontal plane can be seen.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A device for generating sensory stimuli for a child, comprising:
a body made of an elastic material,
a lying area for a child on the body,
at least one first bladder for generating a vertical movement of the lying area and at least one second bladder,
wherein the at least one first bladder and the at least one second bladder are embedded in the elastic material,
wherein a position of the at least one first bladder in the body corresponds substantially to a position of an area of a body of a mother that is moved by breathing and a position of the at least one second bladder in the body corresponds substantially to a position of a heart in the body of the mother, such that the vertical movements of the at least one first bladder simulates a breathing motion of the mother and movements of the at least one second bladder simulates a heartbeat of the mother, and
wherein the at least one first bladder is elongated, such that the at least one first bladder extends along at least one side of the body.

2. The device according to claim 1, wherein the elastic material of the body has a mass density that is similar to that of a human body or of muscle or fatty tissue of the human body and deviates from it by no more than 20%.

3. The device according to claim 1, wherein the elastic material of the body enables a uniform temperature control of the body in an incubator.

4. The device according to claim 1, wherein the elastic material of the body contains polyurethane rubber, polyurethane gel, latex, or another elastic material.

5. The device according to claim 1, wherein the body has no further hollow spaces, apart from positions of the at least one first bladder and the at least one second bladder.

6. The device according to claim 1, wherein the at least one first bladder and the at least one second bladder are enclosed on all sides by the elastic material of the body, and the device further comprising:
an elastic film on an outer surface of the body, which forms at least the lying area.

7. The device according to claim 6, wherein the body is produced by a casting process, in which the elastic material of the body is connected by material bonding with the elastic film and with the at least one first bladder and the at least one second bladder over an entire surface or substantially over the entire surface of the body.

8. The device according to claim 6, wherein the elastic film has polyurethane or polycarbonate or a similar elastic material.

9. The device according to claim 6, wherein a material of the body, a material of the elastic film and a material of the at least one first bladder and the at least one second bladder is transparent to x-rays.

10. The device according to claim 6, wherein a material of the body, a material of the elastic film and a material of the at least one first bladder and the at least one second bladder is transparent or translucent to visible light and/or ultraviolet light.

11. The device according to claim 1, wherein the at least one first bladder is made as two parts or as a pair.

12. The device according to claim 1, wherein two first bladders are provided and are positioned at two opposing sides of the lying area, wherein the at least one second bladder is positioned in a central area of the lying area, such that the at least one second bladder is positioned between the two first bladders, and wherein both of the two first bladders respectfully extend along the two opposing sides of the body.

13. The device according to claim 1, wherein the body further includes at least one speaker and at least one microphone provided therein.

14. The device according to claim 1, further comprising an edge region that projects vertically around a circumferential edge of the body, where the edge region partially overlaps with the at least one first bladder in a top view of the lying area.

* * * * *

UNITED STATES PATENT AND TRADEMARK OFFICE
CERTIFICATE OF CORRECTION

PATENT NO.         : 9,604,029 B2
APPLICATION NO.    : 14/270059
DATED              : March 28, 2017
INVENTOR(S)        : Anabalón Alamos et al.

Page 1 of 1

It is certified that error appears in the above-identified patent and that said Letters Patent is hereby corrected as shown below:

On the Title Page

(72) Inventors shows: Camilo Andres Anabalón Alamos, Stuttgart (DE); Ralph Patrick Manfred Lang, Aichtal (DE)

(72) Inventors should show: Camilo Andres Anabalón Alamos, Aichtal (DE); Ralph Patrick Manfred Lang, Aichtal (DE)

Signed and Sealed this
Sixteenth Day of May, 2017

Michelle K. Lee
*Director of the United States Patent and Trademark Office*